(12) United States Patent
Burgo et al.

(10) Patent No.: US 10,479,756 B2
(45) Date of Patent: Nov. 19, 2019

(54) DIESTERS FOR PERSONAL CARE APPLICATIONS DERIVED FROM 1-METHYLHEPTYL ALCOHOL

(71) Applicant: Inolex Investment Corporation, Wilmington, DE (US)

(72) Inventors: Rocco Burgo, Mullica Hill, NJ (US); Daniel Winn, Kingston, NJ (US)

(73) Assignee: Inolex Investment Corporation, Wilmington, DE (US)

( * ) Notice: Subject to any disclaimer, the term of this patent is extended or adjusted under 35 U.S.C. 154(b) by 0 days.

(21) Appl. No.: 15/482,380

(22) Filed: Apr. 7, 2017

(65) Prior Publication Data

US 2017/0291868 A1    Oct. 12, 2017

Related U.S. Application Data

(60) Provisional application No. 62/319,620, filed on Apr. 7, 2016.

(51) Int. Cl.

| C07C 69/40 | (2006.01) |
|---|---|
| A61K 8/37 | (2006.01) |
| A61K 8/92 | (2006.01) |
| A61Q 19/00 | (2006.01) |
| A61Q 19/04 | (2006.01) |
| A61Q 1/04 | (2006.01) |
| A61Q 19/08 | (2006.01) |
| A61Q 19/10 | (2006.01) |
| A61Q 15/00 | (2006.01) |
| A61Q 3/00 | (2006.01) |
| A61Q 1/14 | (2006.01) |
| A61Q 1/02 | (2006.01) |

(52) U.S. Cl.
CPC ............... *C07C 69/40* (2013.01); *A61K 8/37* (2013.01); *A61K 8/922* (2013.01); *A61Q 19/00* (2013.01); *A61Q 1/02* (2013.01); *A61Q 1/04* (2013.01); *A61Q 1/14* (2013.01); *A61Q 3/00* (2013.01); *A61Q 15/00* (2013.01); *A61Q 19/04* (2013.01); *A61Q 19/08* (2013.01); *A61Q 19/10* (2013.01)

(58) Field of Classification Search
CPC .................................................... C07C 69/40
USPC ......................................................... 560/129
See application file for complete search history.

(56) References Cited

U.S. PATENT DOCUMENTS

| 6,008,167 A * | 12/1999 | Appelman | ........... C10M 105/34 |
|---|---|---|---|
| | | | 508/463 |
| 2015/0166926 A1* | 6/2015 | Scherer | ................ C10M 105/36 |
| | | | 508/512 |

FOREIGN PATENT DOCUMENTS

JP            2012020984     *   2/2012   ............. C07C 69/24

* cited by examiner

*Primary Examiner* — Deborah D Carr
(74) *Attorney, Agent, or Firm* — Calderone Bullock LLC

(57) ABSTRACT

The invention includes a diester exhibiting improved hydrolytic stability that is an esterification product of a 1-methylheptyl alcohol and a dicarboxylic acid. In some embodiments, the diester is bis(1-methyl heptyl) butanedioate, bis(1-methyl heptyl) nonanedioate and/or bis(1-methyl heptyl) decanedioate. The diester may be natural and/or not sourced from palm. Also contemplated within the scope of the invention are diesters exhibiting improved hydrolytic stability represented by Formula (I):

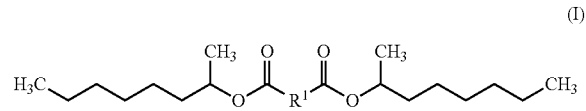

wherein $R^1$ is chosen from a linear alkyl group containing four to ten carbon atoms. Also included are personal care compositions comprising any of these diesters and methods of preparing a personal care composition using the inventive diesters, and/or methods of altering the tactile impression and/or skinfeel provided to a user by a personal care composition by combining any of the diesters of the invention and at least one personal care component to form a personal care composition; and topically applying the personal care composition to the hair, skin, and/or nails of a user.

28 Claims, No Drawings

DIESTERS FOR PERSONAL CARE APPLICATIONS DERIVED FROM 1-METHYLHEPTYL ALCOHOL

CROSS REFERENCE TO RELATED APPLICATIONS

This application claims the benefit under 35 U.S.C. § 119(e) of U.S. Provisional Patent Application No. 62/319,620, filed Apr. 7, 2016, entitled "Diesters for Personal Care Applications Derived from 1-Methylheptyl Alcohol," the entire disclosure of which is incorporated herein by reference.

BACKGROUND OF THE INVENTION

As the population becomes aware of the potential adverse effects to the body and to the environment associated with use of ingredients derived from fossil fuels, the personal care industry has advanced its search for "natural" ingredients. Although the term "natural" currently has no industry standard definition, efforts are under way by industry trade organizations to devise a more uniform, concise meaning. Currently, it is generally recognized that materials derived from renewable and/or sustainable or otherwise non-fossil fuel sources, are considered to be natural. Personal care compositions containing these materials may be marketed accordingly. Currently, it is the industry consensus that petrochemicals and petrochemically-derived materials are not "natural". Compounds made by certain chemical processes may also be considered unsuitable for use in "natural" personal care compositions.

In skin care, the tactile impression or skin feel of a product, such as the feeling upon initial application (initial feel), the feeling during spreading of the product over the skin (rub-out), and the feeling after application is complete (after feel), contribute to the product's commercial success or failure. Other characteristics, such as fragrance and taste or lack thereof, may be equally important. Generally, emollients are the components of a composition that are directly related to the "feel" or tactile impression properties, because they provide lubrication, humectancy, and occlusion.

The spreading rate and viscosity are properties of an emollient that contribute to skin feel or tactile impression. Rapidly spreading/low viscosity products are perceived as "light", whereas slow spreading/higher viscosity products are perceived as "heavy." While heavy feeling products are sometimes preferred, for example, in skin care products such as massage oils, ointments, and barrier creams, lightness as well as a lack of oiliness and/or greasiness is preferred in many applications. Other terms used to describe lightness of a personal care composition may be "dry," "velvety," and "silky." Additionally, in most instances, it is preferable that the emollient(s) is substantially and/or completely free of color and/or taste. It is also desired that they be non-flammable and toxicologically benign.

Esters have been used widely in personal care and pharmaceutical applications for many years.

Natural ester fats, oils and waxes (vegetable oil emollients) are used in their native state providing emolliency, lubricity, structure, and solvency to personal care applications. Vegetable oil emollients are natural; thus, a personal care formulator preparing a "natural" product may choose a vegetable oil over a naturally derived or petrochemically-derived synthetic, even when the magnitude of benefits realized is lesser as compared to that which would be obtained by use of the petrochemically-derived alternative.

Common vegetable oils used in personal care compositions include coconut oil, corn oil, cottonseed oil, canola oil, olive oil, palm oil, peanut oil, safflower oil, sesame oil, soybean oil, sunflower oil and jojoba oil. The viscosities of exemplary vegetable oils are listed in Table 1. As can be seen, the viscosities of these oils are relatively high, and therefore provide a "heavier" skin feel.

TABLE 1

| Viscosity of Common Vegetable Oils | |
|---|---|
| Common Name | Viscosity, Centistokes at 25° C. |
| Corn Oil | 65 |
| Canola Oil | 67 |
| Olive Oil | 87 |
| Soybean Oil | 69 |
| Jojoba Oil | 130 |

Synthetic esters are compounds that are typically formed from the esterification of fatty acids and alcohols. Many fatty acid and alcohol starting materials are available to the ester chemist, and a tremendous range of variation of properties may be obtained. Exemplary properties are viscosity, melting point, surface tension, reactive index, specific gravity, and viscosity/temperature behavior. Also, by using proper esterification and other purification techniques, pleasing aesthetic properties such as skin feel, and the absence of odor and color may be obtained.

Low viscosity emollients that can deliver a light feeling to the skin can be made using entirely non-petrochemically-derived starting materials; however, the availability of suitable starting materials is limited. For example, monoesters of low viscosity and light skinfeel can be synthesized by esterifying ethanol from fermentation of corn, sugar cane, beets, and/or other plants with fractionated vegetable fatty acids of lower chain length, normally derived from coconut or palm kernel oil. Although this method can provide low viscosity, the monoesters derived therefrom have a low molecular weight and tend to be volatile, and therefore odorous, which makes their use limited.

Naturally derived light synthetic esters for use in personal care compositions may also be derived from the esterification of glycerol from vegetable sources with fractionated vegetable derived fatty acids of lower chain length. The most common of these is glyceryl tricaprylate/caprate (Lexol GT 8/65, Inolex Chemical Company, Philadelphia, Pa., USA.) in which the capric and caprylic acid is obtained from splitting and fractionation of coconut or palm kernel oil. The glyceryl tricaprate/tricaprylate material has a viscosity of approximately 25-30 centistokes (at 25° C.) and a spreading value of 2.9 (5 minutes, cm$^2$) and has been characterized as having a light skin feel.

Many starting materials derived from petrochemical origins may be used to produce synthetic esters. However, the principle remains that odorless, lower viscosity synthetic esters having higher spreading values are considered preferable when one wishes to devise a formulation providing a light skin feel. For this reason, often petrochemically-derived materials fitting this definition are selected for use over any glyceryl tricaprylate/caprate material or other natural materials, since these natural materials do not provide the same performance benefits. Examples of such petrochemically-derived synthetic esters widely used within the personal care industry are neopentyl glycol diheptanoate (LexFeel 7, Inolex Chemical Company, Philadelphia, Pa., USA) and isononyl isononanoate (Dermol 99, Alzo International, Sayreville, N.J., USA.) U.S. Pat. Nos. 4,322,545, 4,323,693, and 4,323,694 to Scala, and U.S. Pat. No. 6,365,629 to Zofchak et. al, incorporated herein by reference, also describe wholly or partially petrochemically-derived esters useful in personal care formulations for providing "dry emolliency" and/or "light feeling" to the formulation.

Although there are many chemical pathways to form esters, the most common chemical reaction is typically the direct condensation of a carboxylic acid and an alcohol to yield an ester and water.

This reaction is reversible and will go to about twenty to eighty percent conversion until equilibrium is reached, depending upon the starting materials used. To achieve higher levels of conversion, the water of reaction is removed so that only the forward reaction prevails. Hydrolysis is the reverse reaction wherein the ester reacts with water to form the parent acid and alcohol. Hydrolysis of esters may be catalyzed by acid or alkali. Since pH is a measure of acid or alkali concentration, the kinetic rate of hydrolysis increases as the system pH deviates from neutrality, downward or upward.

In many personal care applications, the final form of the product contains water. Depending on the solubility of water in the phase containing the ester, the pH, and the fundamental strength of the ester linkage, the rate of hydrolysis will be affected.

The fundamental strength of the ester linkage is mainly affected by stearic factors. Alkyl substituents in close proximity to the ester linkage hinder attack on the linkage by water, and thus the rate of hydrolysis is slowed. For example, it has been reported that the alkaline hydrolysis rate constant (kOH, M-1 min-1) for ethyl benzoate and isopropyl benzoate are 15.5 and 3.2 respectively at 60° C. (Larsen and Johansen, 1985.) The isopropyl ester rate under these conditions was about five times lower than that of the ethyl ester illustrating the effect of stearic crowding.

When an ester hydrolyzes, the parent alcohol(s) and acid(s) is(are) released. The molecular weight of the products of cleavage (alcohol and/or acid) are lower than the molecular weight of the ester. For this reason, in many cases the vapor pressure of the parent alcohol and/or acid is higher than that of the ester, and the compounds are volatile enough to create stimulate olfactory nerves, and an odor that can be disagreeable is observed. For this and other reasons, more hydrolytically stable esters may be preferred.

Recent demand for palm oil has expanded due to its increased use in fuel, food, toiletry and other personal care applications. The primary palm plantations are located in Southeast Asia, and particularly in Malaysia and Indonesia. This strong increase in demand has led to deforestation, as many forests have been destroyed to make room for the growing of palm. This has led to increased carbon emissions due to the practice of burning to rapidly induce deforestation. It has also led to microclimate changes in the region as dense forests that retain water are replaced with open palm plantations. Also, deforestation has reduced the available habitat for species such as the orangutan. For this reason, products that are not derived from palm ("palm-free" or "not palm-sourced") may be preferred.

Accordingly, there is a need in the art for esters that can provide a light skin feel when incorporated as an emollient into personal care formulations. Furthermore, there is a need in the art for esters that can provide a light skin feel when incorporated as an emollient into personal care formulations and which meet the current "natural" standard. Ideally, such materials would have viscosities and spreading values similar to the petrochemical alternatives. Furthermore, the esters would preferably be hydrolytically stable, low odor, have good odor stability, and not be derived from palm vegetable sources.

BRIEF SUMMARY OF THE INVENTION

The invention includes a diester exhibiting improved hydrolytic stability that is an esterification product of a 1-methylheptyl alcohol and a dicarboxylic acid. In some embodiments, the diester is bis(1-methyl heptyl) butanedioate, bis(1-methyl heptyl) nonanedioate and/or bis(1-methyl heptyl) decanedioate. The diester may be natural and/or not sourced from palm.

Also contemplated within the scope of the invention are diesters exhibiting improved hydrolytic stability represented by Formula (I):

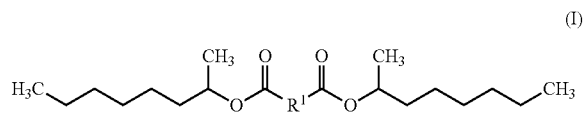

wherein $R^1$ is chosen from a linear alkyl group containing four to ten carbon atoms.

Included as well are personal care compositions comprising any of these diesters.

Methods within the scope of the invention include methods of preparing a personal care composition using the inventive diesters, and/or methods of altering the tactile impression and/or skinfeel provided to a user by a personal care composition by combining any of the diesters of the invention and at least one personal care component to form a personal care composition; and topically applying the personal care composition to the hair, skin, and/or nails of a user. The user perceives a skinfeel or tactile impression of lightness, dryness or silkiness.

DETAILED DESCRIPTION OF THE INVENTION

The invention advantageously provides a solution for personal care formulators wishing to create products having a light skin feel and are pleasant to use. It also provides such benefits by providing such products that are natural, ethically and environmentally responsible.

The inventive diesters that enable this goal, as well as compositions and methods using the diesters are described herein.

"Natural diacids" or "natural dicarboxylic acids", as used herein, means those derived entirely from non-petrochemical carbon containing starting materials. Exemplary natural diacids are butanedioc derived from the fermentation of wheat, nonanedioc acid derived from the ozonolysis of oleic acid, and decanedioic acid derived from the alkali pyrolysis of castor oil. None of the disclosed natural acids for use in the invention are derived from palm. However, used of palm-sourced diacids is not excluded, especially if the palm source is demonstrably ethical and environmentally responsible.

In an embodiment of the invention, it is preferred that 1-methylhepty alcohol is obtained from the alkali pyrolysis of castor oil. Other sources may be contemplated, especially if the source is demonstrably ethical and environmentally responsible.

Synthesis and manufacturing of the initial reactants and/or the diester of the invention may be conducted by any methods known in the art. Most commonly, the esters are prepared by thermal esterification using no catalyst, or a mineral acid catalyst. Post esterification unit operations such as distillation, liquid-liquid extraction, adsorption, and filtration are often employed.

The invention includes a diester for topical application, personal care compositions containing one or more of these diesters, various methods of preparing a personal care composition including the one or more of these diesters, and methods of altering the skin feel and/or tactile impression provided to a user by a personal care composition by including the diester of the invention.

The diesters of the invention and or the reactants that form them may be petrochemically or naturally derived, and can be used to prepare personal care compositions that are partially or wholly natural. By "natural" it is meant that ingredients are wholly derived from renewable and/or sustainable sources, and are not derived from fossil fuels or any other petrochemical sources.

The invention includes diesters for topical application to epidermal, mucosal, and/or keratinized surfaces or tissues such as the skin, hair and/or nails. The diester, the methods, and/or the compositions described herein may be used for topical application to such surfaces/tissues of humans, of animals, and/or for application to animal-derived or plant-derived textiles, furs or skins.

The diesters of the invention exhibit hydrolytic stability in aqueous environments, can be natural and responsibly obtained (e.g., without participation in the palm forestry industry), exhibit viscosities and spread rates comparable to petrochemically derived materials, and provide to the end user a light skinfeel.

The diesters include the esterification product of at least one diacid acid or one alcohol that is derived from a natural source. By "natural source", it is meant that the starting diacid is derived from a renewable and/or a sustainable resource, and not derived from fossil fuel or any other petrochemical sources. For example, the starting acid may be derived from a vegetable oil, such as those obtained from oil-bearing seeds or other botanical source. Without limitation, exemplary oils include almond oil, castor oil, coconut oil, corn (maize) oil, cottonseed oil, canola oil, flax seed oil, hempseed oil, nut oil(s), olive oil, palm oil, peanut oil, safflower oil, sesame oil, soybean oil, sunflower oil, jojoba oil and combinations of these oils. In an embodiment, preferably the starting diacid is derived from castor oil and/or not palm derived.

The diesters of the invention are prepared by esterifying the acid described above with a 1-methylheptyl alcohol. The 1-methylheptyl alcohol is derived from castor oil. Other sources may be contemplated, especially if the source is demonstrably ethical and environmentally responsible. It may be preferred that the 1-methylheptyl alcohol is not palm sourced.

In an embodiment, the ester is prepared from a vegetable-derived diacid that contains 4-10 carbon atoms, or 5, 6, 7, 8, 9, or 10 carbons atoms with 1-methylheptyl alcohol. In some embodiments, the resultant esterification product is bis (1methylheptyl)alkanedioate.

In some embodiments, it may be preferred that the diacid is a linear diacid.

It may be preferred that the resultant diester is substantially free of or free of petrochemical carbon atoms, that is, the carbon atoms in its structure are not directly derived from a petrochemical.

In an embodiment, the ester is a compound represented by the Formula (I).

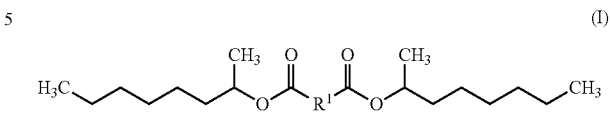

(I)

In formula (I), $R^1$ is a linear alkyl group. The alkyl group may contain four to ten carbon atoms. However, it may be preferred that the alkyl group of $R^1$ is a group having four, nine or ten carbon atoms. Alternatively, it may be preferable that $R^1$ is chosen from an alkyl group having four carbon atoms.

In an embodiment, it may be preferred that $R^1$ is derived from a vegetable carbon source such as wheat or castor oil, such as, for example, butanedioic acid, nonanedioic acid, and decanedioic acid.

The selected acids may be esterified by any means known or developed in the art. For example, esterification may be accomplished by application of heat in the presence of a catalyst, or in the absence of a catalyst, using an excess of the more volatile alcohol component to drive the reaction to high conversion. Neutralization, distillation, adsorption, and filtration processes may be used to purify the product. It may be preferred that the method employed is one that leads to an ester of high purity and low color and odor. Such reactions are well within the skill of a person of ordinary skill in the art and are routinely and conventionally executed in the industry.

The invention also includes personal care compositions that include the diester or diesters.

Personal care compositions may include, but are not limited to, oral care products, skin cleansing products, hair cleansing products, nail preparations (nail polish, nail polish removers, cuticle and/or nail treatments), conditioning agents for skin, nails and hair, antiperspirants and deodorants, soaps, hair sprays, gels, hair shampoo, hair conditioner, pomades, powders, cosmetics, compositions that are subsequently impregnated into textiles for cleansing or other purposes, lipstick, lotions for skin and hair, including those containing sunscreens or UV absorbers, bath or shower oils, lip gloss, lipsticks, cosmetics for use in pigmenting the eye area, such as eyebrow pencils or powders, eye shadows, and eye liners, hand lotions and salves, creams and lotions for the facial area, hair creams, mousses, gels, and other styling aids, mascara, foundations for application to the face, tanning products, and the like. The personal care composition may contain any additional additives or components useful in formulating a product with the desired end benefits. In an embodiment, it may be desirable to include one or more vegetable oils in the product, such as, for example, almond oil, castor oil, coconut oil, corn (maize) oil, cottonseed oil, canola oil, flax seed oil, hempseed oil, nut oil, olive oil, palm oil, peanut oil, safflower oil, sesame oil, soybean oil, sunflower oil, jojoba oil and combinations of these oils. Surfactants may be included in the personal care composition, such as, for example, an anionic surfactant, a zwitterionic surfactant, a cationic surfactant, a non-ionic surfactant and combinations of these.

Other exemplary components may include, without limitation, lipids, alcohols, waxes, pigments, vitamins, fragrances, bleaching agents, antibacterial agents, anti-inflammatory agents, antimycotic agents, thickeners, gums, starches, chitosan, polymeric materials, cellulosic materials, glycerin, proteins, amino acids, keratin fibers, fatty acids, siloxanes, botanical extracts, abrasives and/or exfoliants (chemical or mechanical), anticaking agents, antioxidant agents, binders, biological additives, buffering agents, bulking agents, chelating agents, chemical additives, denaturants, external analgesics, film formers, humectants, opacifying agents, pH adjusters, preservatives, propellants, reducing agents, sunscreen agents, skin darkening agents, essential oils, skin sensates, and combinations of these.

Also included in the invention are methods of preparing a personal care composition including combining the diester of the invention with a personal care composition component. Such component may include any known in the art, such as, for example, those listed above. In an embodiment, the preferred component is a vegetable oil or an essential oil. In an embodiment of the invention, methods of altering or modifying the tactile impression and/or skin feel provided to a user by application of an emollient personal care composition are included. Such method includes incorporating an ester and at least one component that is chosen from a conventional personal care ingredient component, such as, for example, a gum, a natural oil, a cellulosic compound, a salt, a wax, and/or any of the other components listed above.

The entire contents of U.S. Patent Application Ser. No. 62/319,620 are herein incorporated into this text by reference.

EXAMPLES

The physical properties of bis(1-methyheptyl)butanedioate are evaluated and compared to one petrochemically-derived ester, and one "natural" ester that are currently used in the art.

Kinematic viscosity was tested at 25° C. using ASTM (American Society of Testing and Materials, West Conshohocken, Pa., USA) official method number D-44515a.

Acid value (AV) was measured using ASTM official method number D-974-14$^{\varepsilon^2}$.

Moisture content (% HOH) was measured using an automatic volumetric Karl-Fischer device, the Aquastar AQV21 (Gibbstown, N.J., USA.)

Color was measured using ASTM D-1209-05(2001 reapproved), and flash point was determined using ASTM D-92-12b.

Odor was evaluated olfactorily by a human subject.

To test the spreading characteristics, 10 ul of test substance is applied as a drop on the volar forearm to six subjects, and the spreading are of the substance is measured after intervals one, three, and five minutes. More rapidly spreading products will have a higher spreading area at each time interval.

Table 2 shows the properties of an exemplary ester of the invention, bis(1-methylheptyl) butanedioate in comparison to glyceryl tricaprylate/caprate, an industry preferred naturally derived ester emollient, and neopentyl glycol diheptanoate, an industry preferred petrochemically-derived ester emollient.

TABLE 2

| Property, Units | bis(1-methylheptyl) butanedioate | glyceryl tricaprylate/ caprate | neopentyl glycol diheptanoate |
|---|---|---|---|
| Kinematic Viscosity, cSt | 12.0 | 27.2 | 7.2 |

TABLE 2-continued

| Property, Units | bis(1-methylheptyl) butanedioate | glyceryl tricaprylate/ caprate | neopentyl glycol diheptanoate |
|---|---|---|---|
| Acid value, mg KOH/g | 0.01 | 0.03 | 0.05 |
| Moisture, wt. % | 0.01 | 0.01 | 0.01 |
| Color, APHA | 12 | 20 | 17 |
| Odor | Mild, Characteristic | Mild, Characteristic | Mild, Characteristic |
| Spreading Area, cm after 1 min. | 2.0 | 1.8 | 2.1 |
| Spreading Area, cm after 3 min. | 2.7 | 2.6 | 3.2 |
| Spreading Area, cm after 5 min. | 3.2 | 2.9 | 3.7 |

Example 1—Self-Tanning Gel

A self-tanning gel is made aesthetically pleasing and ethically acceptable by inclusion of the inventive diester, which provides a light skinfeel without use of palm-sourced ingredients.

To prepare the gel, the Phase I ingredients from Table 3 below are combined by propeller mixing until the Ultragel 300 is hydrated. The pH of the composition is adjusted to about 4, then the composition is heated to about 80° C. Separately, the Phase II ingredients from Table 3 below are combined and heated to 80° C. The Phase II composition is added to the Phase I composition via mixing, and the batch is homogenized @ 3500 rpm for 3 minutes. The batch is cooled. Separately, the Phase III ingredients are combined. When the batch is cooled, the Phase III mixture is added to the batch with mixing. The entire product is then cooled to room temperature.

The end product has a pH of about 4.03 and it is stable at 25° C., 45° C., and 50° C. for at least two weeks.

Its viscosity at 25° C. (Brookfield RVT; Spindle T-C @ 10 rpm) is 20,000 cps.

TABLE 3

| Ingredients | INCI or Chemical Name | WT % |
|---|---|---|
| Phase I | | |
| Deionized Water | Water | 76.5 |
| Ultragel 300 | Polyquaternium-37 | 1.0 |
| Glycerin | Glycerin | 3.0 |
| Phase II | | |
| Sustoleo MCT | Triheptanoin | 8.0 |
| Inventive Substance | Bis(1-methyl-heptyl)butanedioate | 5.0 |
| Sustoleo TSB | *Brassica* Glycerides | 2.0 |
| Phase III | | |
| Lexgard O | Caprylyl Glycol | 0.3 |
| Dihydroxyacetone | Dihydroxyacetone | 3.0 |
| Fragrance | Fresh Floral, 6117421 | 0.5 |
| Total | | 100.0 |

Example 2—Deep Moisturizing Conditioner

The formulation has a deep, moisturizing aesthetic, but the light elegant skin feel is provided by the inventive substance. Separately, the Phase II ingredients from Table 4 below are combined and heated to 80° C. with propeller mixing until uniform. The Phase I composition is added to the Phase II composition and mixed with propeller mixing. The batch is cooled to 65° C. and then homogenized for 3 minutes. Subsequently, the batch is cooled to room temperature.

The end product has a pH of about 5.02 and a viscosity at 25° C. (Brookfield RVT; Spindle T-C @ 10 rpm) is 38,000 cps.

TABLE 4

| Ingredients | INCI or Chemical Name | WT % |
|---|---|---|
| Phase I | | |
| Deionized Water | | 84.4 |
| Aspartic Acid | Aspartic Acid | 0.4 |
| Ultragel 300 | Polyquaternium-37 | 0.2 |
| SustOleo 1822 | Brassicamidopropyl Dimethylamine | 2.0 |
| Lexgard O | Caprylyl Glycol | 1.0 |
| Phase II | | |
| Sustoleo GMS | Glyceryl Stearate | 3.0 |
| SustOleo BG | Brassica Glycerides | 2.0 |
| SustOleo BA | Brassica Alcohol | 1.0 |
| SustOleo MCT | Triheptanoin | 4.0 |
| Inventive Substance | Bis(1-methylheptyl)butanedioate | 2.0 |
| Total | | 100.0 |

Example 3—Soft Matte Lip Color Composition

This lip color composition delivers a soft, velvety matte finish and provides a smooth pay-off on lips. This skin feel is enriched by inclusion of the inventive substance.

To prepare the lip color composition, the Phase I ingredients from Table 5 are combined under heat (85° C.) with mixing until the waxes have melted. Separately, combine Phase II pigments from Table 5 and mill together. Add combined Phase II ingredients into Phase I composition under heat and mix well. Pour batch into heated lipstick mold and cool to room temperature. The product exhibited stability at 45° C.

TABLE 5

| Ingredients | INCI or Chemical Name | WT % |
|---|---|---|
| Phase I | | |
| SustOleo MCT | Triheptanoin | 49.7 |
| Sustoleo BG | Brassica Glycerides | 8.0 |
| Candelilla Wax | Candelilla Wax | 13.0 |
| SustOleo TSB | Tristearin (and) Tribehenin | 3.0 |
| Lexgard O | Caprylyl Glycol | 1.0 |
| Vitamin E Acetate | Tocopherol | 0.5 |
| Phase II | | |
| Inventive Substance | Bis(1-methylheptyl)butanedioate | 10.0 |
| Titanium Dioxide | Titanium Dioxide | 2.0 |
| Gemstone Ruby | Mica (and) Titanium Dioxide (and) Iron Oxide (and) Carmine | 2.0 |
| Carmine | Carmine | 0.8 |
| Mica | Mica | 10.0 |
| Total | | 100.0 |

Example 4—Anti-Aging Cream Cleanser

A cleanser in which the inventive substance provides extremely light, dry skin feel was created. To prepare the cleanser, combine the Phase I ingredients from Table 6 and heat to 80° C. Hold the composition at this temperature for 30 minutes while mixing. Separately, heat the ingredients of Phase II from Table 6 to 80 C, and add to the Phase I mixture. Cool while mixing until the composition is at room temperature. Add Phase III ingredients and mix until uniform.

A sample of the material was held at −4° C. for a period of time, then allowed to thaw and held for some time, then heated to +50° C. for a period of time. This sequence was repeated three times. After this, the characteristics of the sample were evaluated, and compared to material that has not undergone this treatment. In the treated samples, the emulsion remained stable and the texture and appearance had not changed significantly.

TABLE 6

| Ingredients | INCI or Chemical Name | WT % |
|---|---|---|
| Phase I | | |
| Water | Water | 67.8 |
| SustOleo 1822 | Brassicamidoproyl Dimethylamine | 2.0 |
| Glycerin | Glycerin | 3.0 |
| Aspartic Acid | Aspartic Acid | 0.7 |
| Lexaine C | Cocamidopropyl Betaine | 5.0 |
| Lexgard O | Caprylyl Glycol | 1.0 |
| Phase II | | |
| Inventive Substance | Bis(1-methylheptyl)butanedioate | 10.0 |
| SustOleo BA | Brassica Alcohol | 7.0 |
| SustOleo GMS | Glyceryl Stearate | 3.0 |
| Phase III | | |
| Salicylic Acid | Salicylic Acid | 0.5 |
| Lemon Verbena Extract | Lemon Verbena Extract | 1.0 |
| Jojoba Floraesters | Jojoba Floraesters | 3.0 |
| Total | | 100.00 |

Example 5—Antiperspirant Stick

A basic anti-perspirant stick wherein the inventive substance is completely stable to hydrolysis is prepared as follows: The Phase I ingredients from Table 7 below were combined and heated to 80° C. until fully melted. The Phase II ingredients were added and the entire mixture was mixed until uniform. The composition was poured into molds and allowed to cool. Hydrolytic stability for at least 1 month at each of 45° C. and 50° C. was observed.

Example 6—All Natural, Palm Free BB Cream

This anhydrous all natural and palm free BB cream provides impeccable skin softening as well as light buildable coverage.

The cream was prepared by combining all Phase I ingredients and melting them under heat until the mixture was uniform. All Phase II pigments were pre-milled together until of uniform size; they were then dispersed into the Phase I composition. The entire composition was homogenized at 3.5 rpm for 5 minutes, and mixed using a propeller mixer until cool. The resultant product was a viscous gel-like beige balm.

TABLE 8

| Ingredients | INCI or Chemical Name | WT % |
|---|---|---|
| Phase I | | |
| Inventive Substance | Bis(1-methylheptyl)butanedioate | 55.0 |
| Sunflower seed oil | *Helianthus Annuus* (Sunflower) Seed Oil | 3.0 |
| Olive oil | *Olea Europaea* (Olive) Fruit Oil | 2.0 |
| Coconut oil | *Cocos Nucifera* (Coconut) Oil | 2.0 |
| Shea butter | *Butyrospermum Parkii* (Shea) Butter | 2.0 |
| Jojoba seed oil | *Simmondsia Chinensis* (Jojoba) Seed Oil | 2.0 |
| Tamanu seed oil | *Calophyllum Inophyllum* (Tamanu) Seed Oil | 1.0 |
| Soybean oil | *Glycine Soja* (Soybean) Oil | 1.0 |
| Carrot fruit oil extract[2] | Carrot Fruit Oil Extract | 1.0 |
| Vitamin E | Tocopheryl Acetate (Vitamin E) | 1.0 |
| SustOleo BG | *Brassica* Glycerides | 7.0 |
| Preservative | Preservative | 1.0 |
| Kaolin | Kaolin White Clay | 10.0 |
| Phase II | | |
| Titanium Dioxide | Titanium Dioxide Oil Dispersible | 8.0 |
| Mica | Sericite Mica | 2.5 |
| Unipure Yellow LC125 | Iron Oxides | 0.9 |
| Unipure Red LC381 | Iron Oxides | 0.4 |
| Unipure Black LC989 | Iron Oxides (and) Triethoxycaprylylsilane | 0.2 |
| Total | | 100.00 |

Example 7—Nail Strengthening Liquid

A blend of light emollients and oils, enriched with vitamins, designed to penetrate and protect nails and cuticle area was prepared. The ingredients in Table 9 were combined and mixed until uniform. The resultant product was a low viscosity liquid.

TABLE 9

| Ingredient | INCI or Chemical Name | WT % |
|---|---|---|
| Inventive Substance | Bis(1-methyl-heptyl)butanedioate | 91.0 |
| Alcohol SDA 40B | Alcohol | 5.0 |
| Jojoba Oil | *Simmondsia Chinensis* (Jojoba) Seed Oil | 2.0 |
| Vitamin E | Tocopherol | 0.5 |
| Panthenol | Panthenol | 0.5 |
| Fragrance | Fragrance | 1.0 |
| Total | | 100.0 |

Example 8—Cleansing Oil

A luxurious cleansing oil that instantly melts away make up and dirt was prepared. To use, the consumer massages the oil into dry skin and rinses away impurities and residue.

To prepare the oil, the ingredients of Table 10 were combined and mixed until uniform. The resulting product was a low viscosity liquid.

TABLE 10

| Ingredient | INCI or Chemical Name | WT % |
|---|---|---|
| Inventive Substance | Bis(1-methyl-heptyl)butanedioate | 87.5 |
| Olive Oil | *Olea Europaea* | 5.0 |
| Sunflower Oil | *Helianthus Annuus* | 3.0 |
| Vitamin E Acetate | Tocopheryl Acetate | 0.5 |
| Carrot Root Extract | — | 2.0 |
| Lexgard O | Caprylyl Glycol | 1.0 |
| Fragrance | — | 1.0 |
| Total | | 100.0 |

Example 9—Night Serum

The night serum was prepared by combining all ingredients of Table 11, heating them until all solids have melted, and mixing the composition until uniform while cooling to room temperature.

A sample of the material was placed in 45° C. and 50° C. oven and held for 2 weeks. After this, the properties of the material such as texture, uniformity, odor, etc. were evaluated against material held at room temperature. The properties were not significantly different. The resultant product was a low viscosity liquid.

TABLE 11

| Ingredients | INCI or Chemical Name | WT % |
|---|---|---|
| Inventive Substance | Bis(1-methylheptyl)butanedioate | 79.0 |
| SustOleo MCT | Triheptanonin | 10.0 |
| SustOleo TSB | *Brassica* Glycerides | 5.0 |
| SustOleo QMS | Glyceryl Stearate | 4.0 |
| SustOleo BG | *Brassica* Glycerides | 1.0 |
| Lexgard O | Caprylyl Glycol | 1.0 |
| Total | | 100.00 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A diester exhibiting improved hydrolytic stability that is an esterification product of a 1-methylheptyl alcohol and a dicarboxylic acid.

2. The diester of claim 1, wherein the dicarboxylic acid is linear.

3. The diester of claim 1 wherein the dicarboxylic acid contains four to ten carbon atoms.

4. The diester of claim 1, wherein the dicarboxylic acid contains 5, 6, 7, 8, 9, or 10 carbon atoms.

5. The diester of claim 1 wherein the dicarboxylic acid contains 7 to 10 carbon atoms.

6. The diester of claim 1, wherein the diester is substituted.

7. The diester of claim 1, wherein the dicarboxylic acid is substantially free of petrochemical carbon atoms.

8. The diester of claim 1 wherein neither the dicarboxylic acid nor the 1-methylheptyl alcohol is a palm derivative.

9. The diester of claim 1 that is bis(1-methyl heptyl) butanedioate, bis(1-methyl heptyl) nonanedioate and/or bis(1-methyl heptyl) decanedioate.

10. The diester of claim 1 that is bis(1-methyl heptyl) butanedioate.

11. The diester of claim 1, wherein the dicarboxylic acid is butanedioic acid.

12. The diester of claim 11, wherein the butanedioic acid is derived from a plant source.

13. The diester of claim 12, wherein the plant source is wheat.

14. The diester of claim 1 wherein the dicarboxylic acid is derived from a plant source.

15. The diester of claim 1, wherein the 1-methylheptyl alcohol is derived from castor oil.

16. The diester of claim 1 represented by the Formula (1):

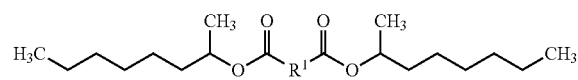

(I)

wherein R$^1$ is chosen from a linear alkyl group containing four to ten carbon atoms.

17. A diester exhibiting improved hydrolytic stability represented by Formula (I):

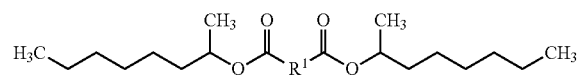

(I)

wherein R$^1$ is chosen from a linear alkyl group containing four to ten carbon atoms.

18. The diester of claim 17 wherein R$^1$ is chosen from a linear alkyl group containing 5, 6, 7, 8, or 9 carbon atoms.

19. A personal care composition comprising the diester of claim 1.

20. The personal care composition of claim 19, further comprising at least one vegetable oil.

21. The personal care composition of claim 20 wherein the vegetable oil is selected from almond oil, castor oil, coconut oil, corn (maize) oil, cottonseed oil, canola oil, flax seed oil, hempseed oil, nut oil, olive oil, palm oil, peanut oil, safflower oil, sesame oil, soybean oil, sunflower oil, jojoba oil, and combinations thereof.

22. The personal care composition of claim 19, further comprising at least one component selected from an anionic surfactant, a zwitterionic surfactant, a cationic surfactant, a non-ionic surfactant, and combinations thereof.

23. The personal care composition of claim 19 further comprising at least one of a water, a lipid, an extract, a floral water, an alcohol, a wax, an anionic emulsifier, a cationic emulsifier, a nonionic emulsifier, a pigment, a vitamin, a fragrance, a bleaching agent, an antibacterial agent, an anti-inflammatory agent, an antimycotic agent, a thickener, a starch, chitosan, a polymeric material, a cellulosic material, glycerin, a protein, an amino acid, a keratin fiber, a fatty acid, a siloxane, an abrasive, an exfoliant, an anticaking agent, an antioxidant agent, a binder, a biological additive, a biologic, lanolin, a buffering agent, a bulking agent, a chelating agent, a chemical additive, a denaturant, an external analgesic, a film former, an humectant, an opacifying agent, a pH adjuster, a preservative, a propellant, a reducing agent, a sunscreen agent, a skin darkening agent, an essential oil, a skin sensate, and combinations thereof.

24. The personal care composition of claim 19, wherein the composition is substantially free of petrochemically derived compounds.

25. A method of preparing a personal care composition comprising combining the diester of claim 1 and at least one component of a personal care composition.

26. The method of claim 25, wherein the at least one component is selected from an anionic surfactant, a zwitterionic surfactant, a cationic surfactant, a non-ionic surfactant, a lipid, an alcohol, a wax, a pigment, a vitamin, a fragrance, a bleaching agent, an antibacterial agent, an anti-inflammatory agent, an antimycotic agent, a thickener, a starch, chitosan, a polymeric material, a cellulosic material, glycerin, a protein, an amino acid, a keratin fiber, a fatty acid, a siloxane, an abrasive, an exfoliant, lanolin an anticaking agent, an antioxidant agent, a binder, a biological additive, a buffering agent, a bulking agent, a chelating agent, a chemical additive, a denaturant, an external analgesic, a film former, an humectant, an opacifying agent, a pH adjuster, a preservative, a propellant, a reducing agent, a sunscreen agent, a skin darkening agent, an essential oil, a skin sensate and combinations thereof.

27. The method of claim 25 further comprising admixing the diester with at least one vegetable oil prior to combination with the at least one component.

28. The method of claim 27, wherein the at least one vegetable oil is selected almond oil, castor oil, coconut oil, corn (maize) oil, cottonseed oil, canola oil, flax seed oil, hemp seed oil, nut oil, olive oil, palm oil, peanut oil, safflower oil, sesame oil, soybean oil, sunflower oil, jojoba oil and combinations thereof.

* * * * *